United States Patent
Overmyer et al.

(10) Patent No.: US 10,327,854 B2
(45) Date of Patent: Jun. 25, 2019

(54) ROBOTIC SURGICAL SYSTEM AND METHODS FOR ARTICULATION CALIBRATION

(71) Applicant: Ethicon LLC, Guaynabo, PR (US)

(72) Inventors: Mark D. Overmyer, Cincinnati, OH (US); Jeffrey S. Swayze, West Chester, OH (US); Robert L. Koch, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 170 days.

(21) Appl. No.: 15/422,767

(22) Filed: Feb. 2, 2017

(65) Prior Publication Data
US 2018/0214219 A1 Aug. 2, 2018

(51) Int. Cl.
| A61B 34/30 | (2016.01) |
| A61B 17/00 | (2006.01) |
| B25J 9/16 | (2006.01) |
| A61B 34/00 | (2016.01) |
| A61B 34/37 | (2016.01) |
| A61B 34/35 | (2016.01) |

(52) U.S. Cl.
CPC ........ *A61B 34/30* (2016.02); *A61B 17/00234* (2013.01); *A61B 34/37* (2016.02); *A61B 34/71* (2016.02); *B25J 9/1692* (2013.01); *A61B 34/35* (2016.02); *A61B 2034/305* (2016.02)

(58) Field of Classification Search
CPC ... A61B 17/00234; A61B 34/30; A61B 34/37; A61B 34/71; A61B 34/35; A61B 2034/305; B25J 9/1692
See application file for complete search history.

(56) References Cited

U.S. PATENT DOCUMENTS

| 8,114,345 B2 | 2/2012 | Dlugos, Jr. et al. |
| 2011/0282154 A1* | 11/2011 | Umemoto ............ A61B 1/0051 600/152 |

(Continued)

FOREIGN PATENT DOCUMENTS

| EP | 1815950 A1 | 8/2007 |
| EP | 3109013 A1 | 12/2016 |

(Continued)

OTHER PUBLICATIONS

Written Opinion for Intl. App. No. PCT/IB2018/050557 dated Apr. 26, 2018.

*Primary Examiner* — Rachid Bendidi
(74) *Attorney, Agent, or Firm* — Mintz Levin Cohn Ferris Glovsky and Popeo, P.C.

(57) ABSTRACT

Systems and methods for articulation calibration of a surgical tool configured to be coupled to a robotic surgical system are provided. The tool including a tool shaft with an end effector has at least one linkage member extending along the shaft and operably coupled to the end effector such that force selectively applied to the linkage member is able to cause articulation of the end effector. The tool can also include a homing mechanism. To perform articulation calibration of the end effector, it can be constrained, force can be applied to the linkage member to attempt articulation of the end effector until a resistance against further articulation exceeds a threshold, and a home position of the end effector can be determined based on a force at which the resistance has exceeded the threshold.

15 Claims, 11 Drawing Sheets

(56) References Cited

U.S. PATENT DOCUMENTS

2015/0094737 A1* 4/2015 Hatakeyama .......... A61B 34/30
606/130
2016/0374772 A1* 12/2016 Hasegawa ................ A61B 1/00
606/130

FOREIGN PATENT DOCUMENTS

| WO | WO-2014151621 A1 | 9/2014 |
| WO | WO-2014151952 A1 | 9/2014 |

\* cited by examiner

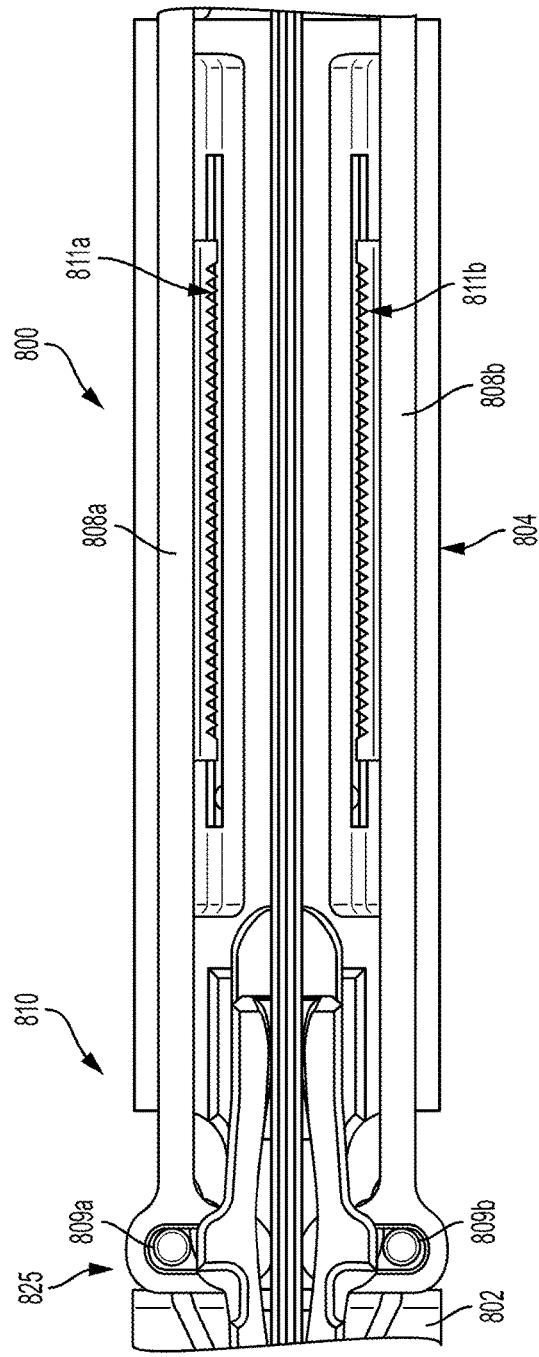
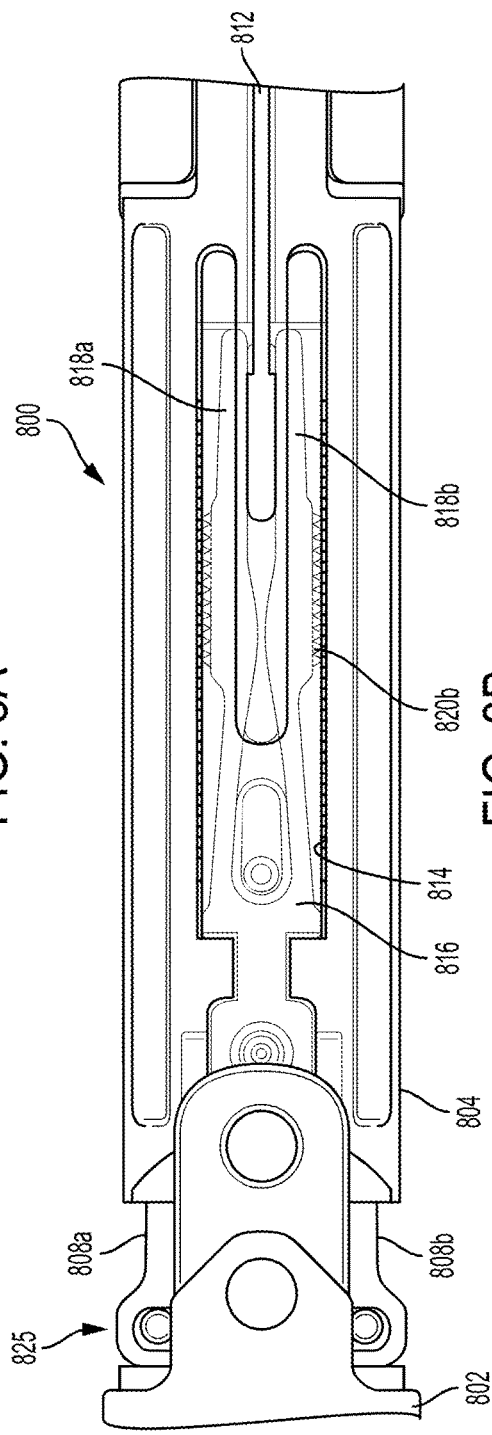
FIG. 8A
FIG. 8B

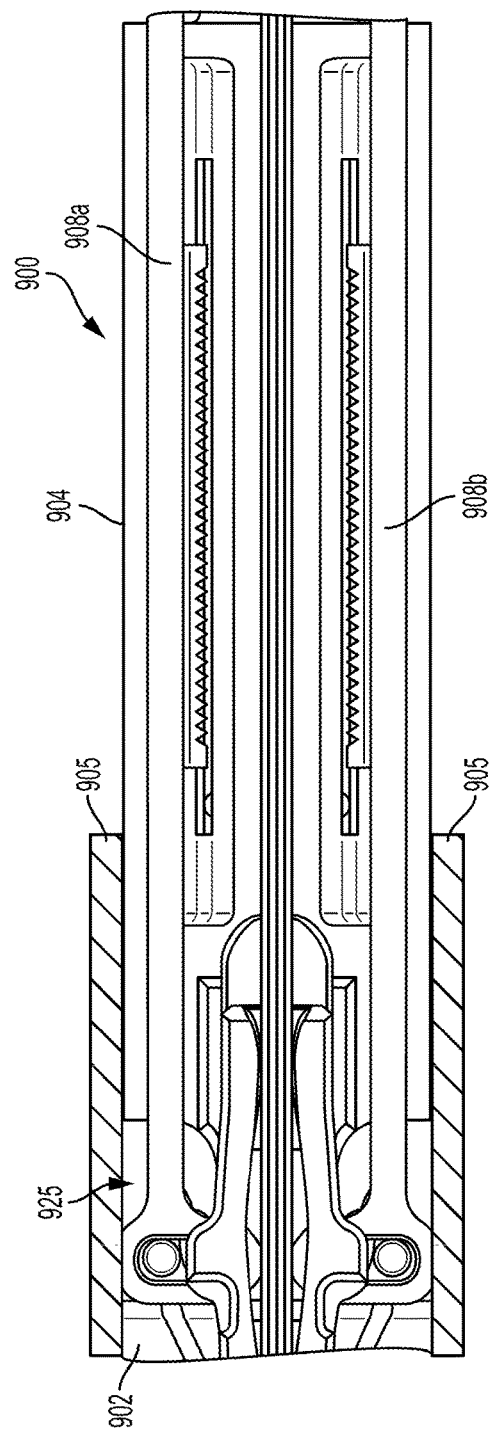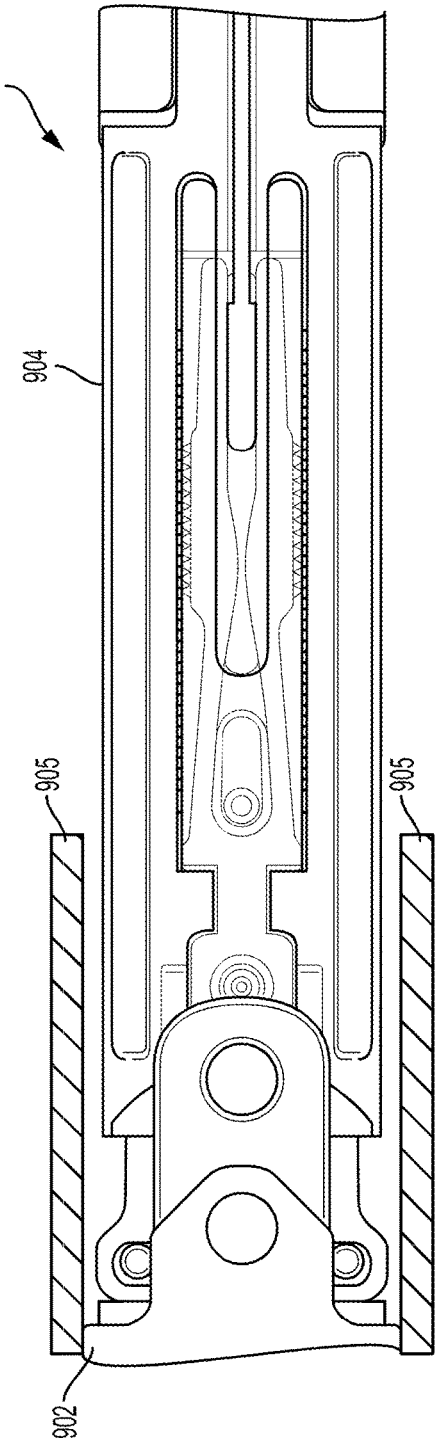
FIG. 9A
FIG. 9B

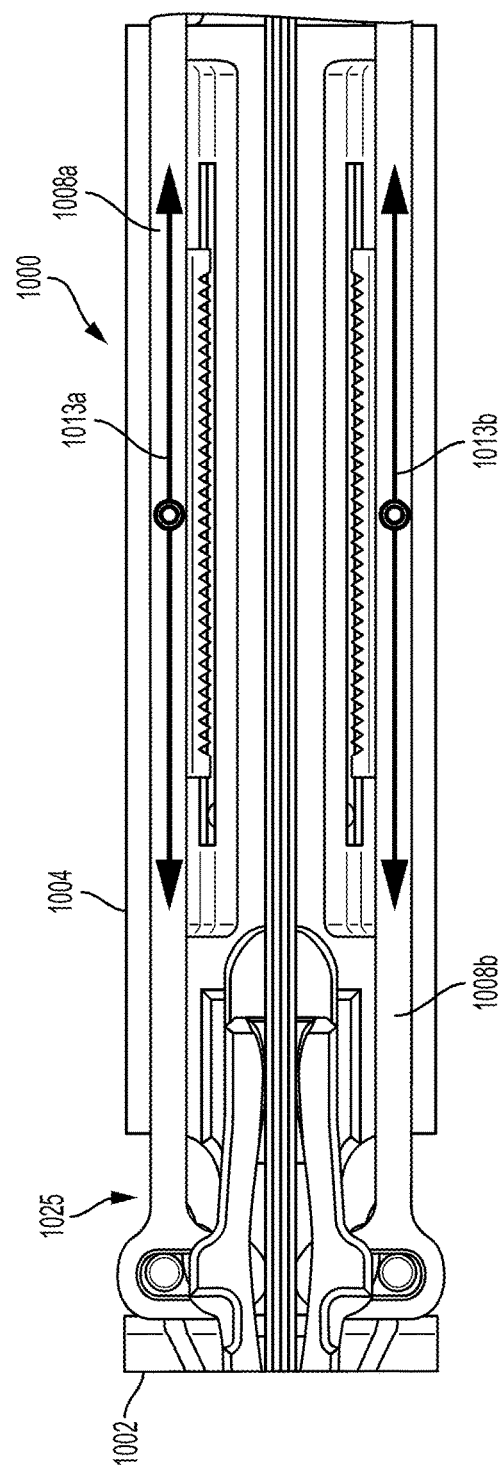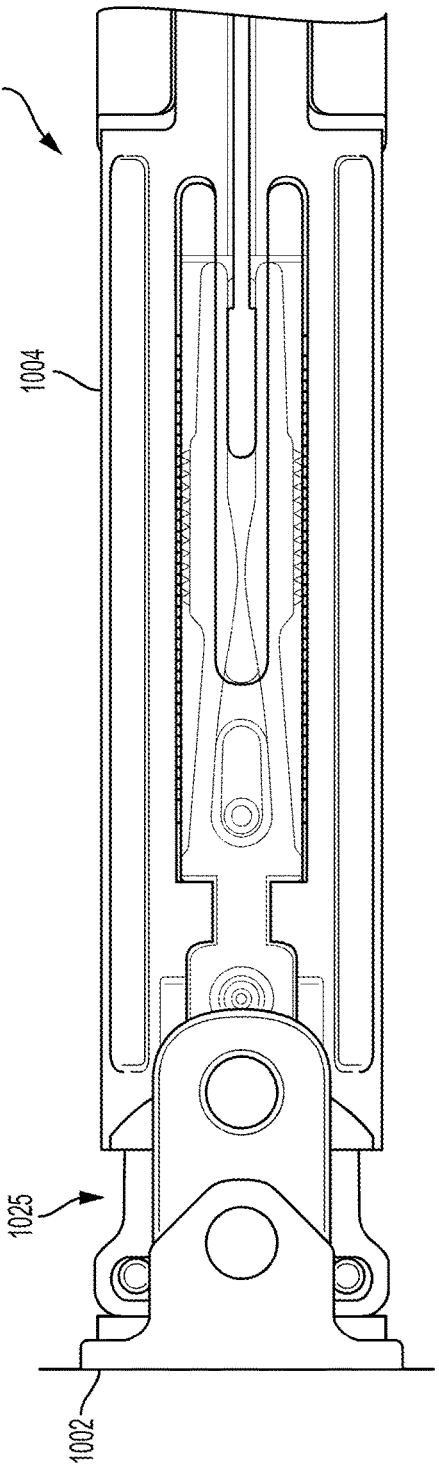
FIG. 10A
FIG. 10B

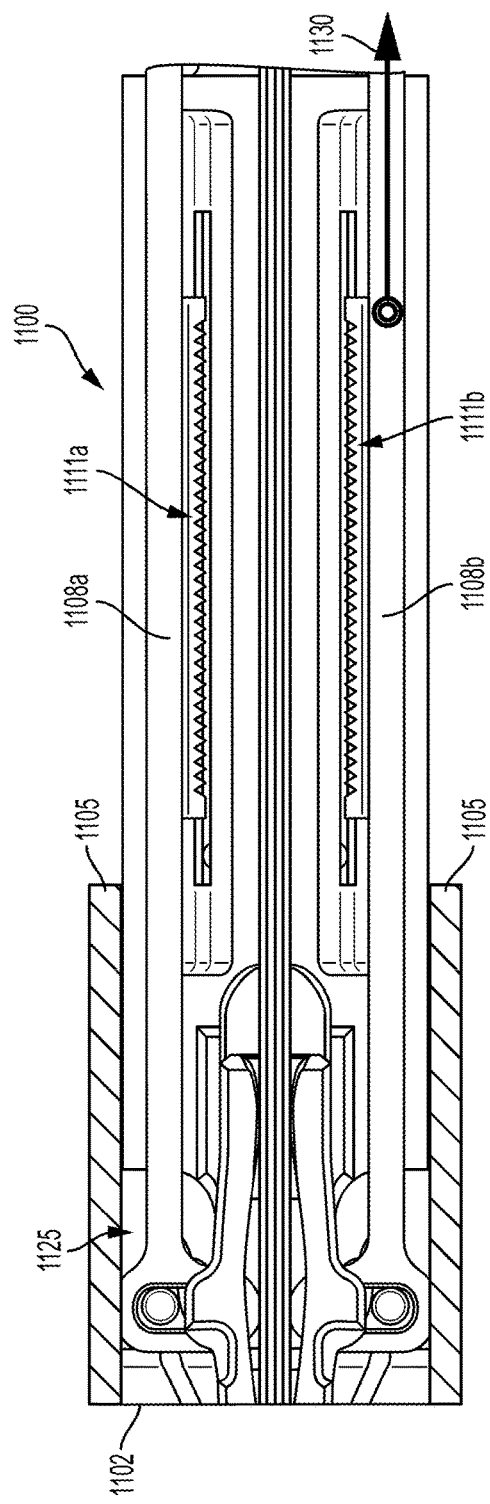
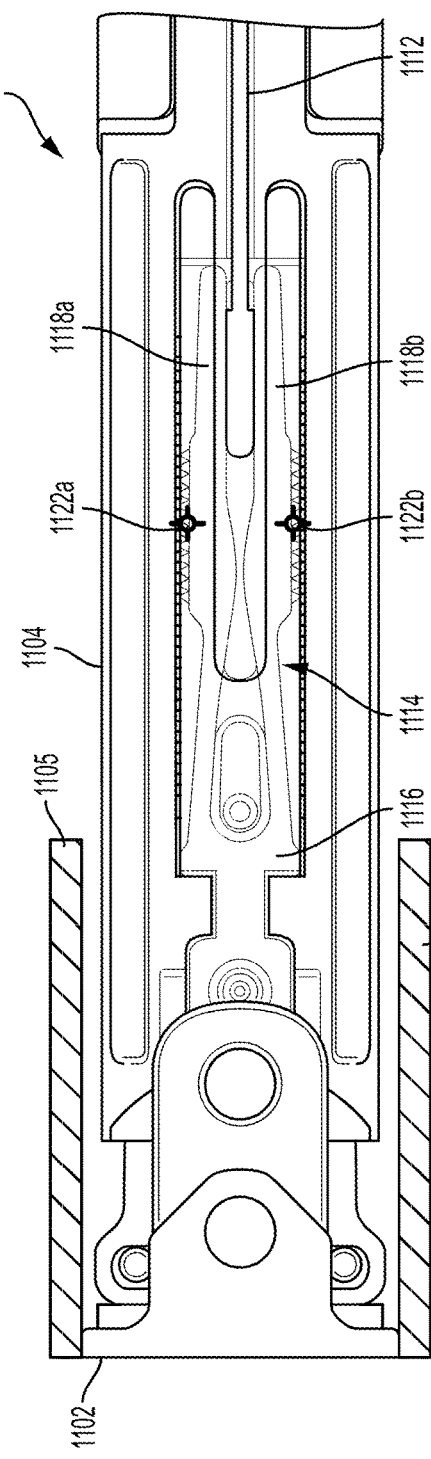
FIG. 11A
FIG. 11B

ROBOTIC SURGICAL SYSTEM AND METHODS FOR ARTICULATION CALIBRATION

FIELD

Methods and devices are provided for robotic surgery, and in particular for calibration of articulating robotic surgical tools.

BACKGROUND

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Although traditional minimally invasive surgical instruments and techniques have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity, and sensitivity of endoscopic tools has been found to be an impediment in the increased the use of minimally invasive surgery.

Over the years a variety of minimally invasive robotic systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient whilst viewing the end effector movement on the visual display during the surgical procedure. While viewing typically a three-dimensional image of the surgical site on the visual display, the surgeon performs the surgical procedures on the patient by manipulating master control devices at the remote location, which master control devices control motion of the remotely controlled instruments.

While significant advances have been made in the field of robotic surgery, there remains a need for improved methods, systems, and devices for use in robotic surgery.

SUMMARY

In general, calibrating robotic surgical tools is provided. Methods and systems capable of detecting a rotational angle of an elongate shaft of a surgical tool are provided.

In one aspect, a surgical method is provided that in some embodiments includes constraining an end effector coupled to a distal end of a shaft of a surgical tool coupled to a robotic surgical system to substantially limit articulation of the end effector relative to the shaft, applying a first force to at least one linkage member operably coupled to the end effector to attempt articulation of the end effector in a first direction until a resistance against further articulation exceeds a first threshold, and storing a first value of a force at which the resistance has exceeded the first threshold, applying a second force to the at least one linkage member to attempt articulation of the end effector in a second, opposite direction until a resistance against further articulation exceeds a second threshold, and storing a second value of a force at which the resistance has exceeded the second threshold, determining first and second articulation angles based on the first and second values, and averaging the first and second articulation angles to obtain a home position of the end effector.

The method can vary in many different ways. For example, the at least one linkage member can include a first linkage member and a second linkage member, the first force can be applied to the first linkage member, and the second force can be applied to the second linkage member. The at least one linkage member can include a plurality of flexible cables.

In some embodiments, determining the first and second articulation angles involves correlating the first and second values with stored values of a force that can be applied to the at least one linkage member, each of the stored values being stored in association with a respective value of an articulation angle. Storing the first and second values can include storing the first and second values in a memory associated with the robotic surgical system.

The method can further include applying a force to the at least one linkage member to cause at least a portion of the end effector to pivot relative to the shaft with reference to the home position of the end effector. The home position of the end effector indicates a position of the end effector at which an articulation angle of the end effector with respect to the shaft is considered to be zero.

In at least some embodiments, constraining the end effector includes actuating a homing member to substantially limit articulation of the end effector relative to the shaft. Further, in at least some embodiments, constraining the end effector includes at least partially inserting the end effector into a trocar to thereby substantially limit articulation of the end effector relative to the shaft.

The first and second thresholds can be predetermined thresholds known to the robotic surgical system.

In another aspect, a surgical tool configured to be coupled to a robotic surgical system is provided. In at least some embodiments, the surgical tool includes a tool shaft having an end effector coupled to a distal end thereof, a wrist disposed between the tool shaft and the end effector, at least one linkage member associated with the tool shaft and operably coupled to the end effector such that force selectively applied to the linkage member is able to cause at least one of a pitch and a yaw motion of the end effector, and a homing mechanism configured to be actuated to angularly adjust a presumed zero position of the end effector relative to the tool shaft to an adjusted zero position of the end effector.

The surgical tool can vary in many different ways. For example, the end effector can be configured to be moved with respect to the wrist with reference to the adjusted zero position. As another example, when the end effector is in the adjusted zero position relative to the tool shaft, the at least one linkage member can be configured to have force applied thereto to attempt articulation of the end effector in at least one direction until a resistance against further articulation exceeds a threshold.

In some embodiments, the at least one linkage member includes a plurality of flexible cables. In some embodiments, the surgical tool further includes a memory configured to store a plurality of values of a force that can be applied to the at least one linkage member, each of the stored values being stored in association with a respective value of an articulation angle.

The homing mechanism can have a variety of different configurations. For example, in at least some embodiments, the homing mechanism includes an elongate element configured to move distally to engage an engagement member associated with the wrist. In at least some embodiments, the homing mechanism comprises a fork member and a push rod configured to move distally into the fork member to cause the fork member to lockingly engage the linkage member. The fork member can have a plurality of teeth configured to engage a plurality of teeth formed on the linkage member. The homing mechanism can be configured to angularly adjust the presumed zero position of the end effector by causing the teeth of the fork member to engage the teeth formed on the linkage member such that the linkage member is disposed at one of a plurality of predetermined positions with respect to the homing mechanism.

BRIEF DESCRIPTION OF THE DRAWINGS

The present disclosure will be more fully understood from the following detailed description taken in conjunction with the accompanying drawings, in which:

FIG. 8A is a perspective view of one side of a homing mechanism of surgical tool configured to be removably coupled to a surgical robotic system;

FIG. 8B is a perspective view of the opposite side of the homing mechanism of FIG. 8A;

FIG. 9A is a perspective view of one side of a homing mechanism of a surgical tool configured to be removably coupled to a surgical robotic system;

FIG. 9B is a perspective view of the opposite side of the homing mechanism of FIG. 9A;

FIG. 10A is a perspective view of one side of a homing mechanism of a surgical tool configured to be removably coupled to a surgical robotic system;

FIG. 10B is a perspective view of the opposite side of the homing mechanism of FIG. 10A;

FIG. 11A is a perspective view of one side of a homing mechanism of a surgical tool configured to be removably coupled to a surgical robotic system;

FIG. 11B is a perspective view of the opposite side of the homing mechanism of FIG. 11A.

DETAILED DESCRIPTION

Figure 1:
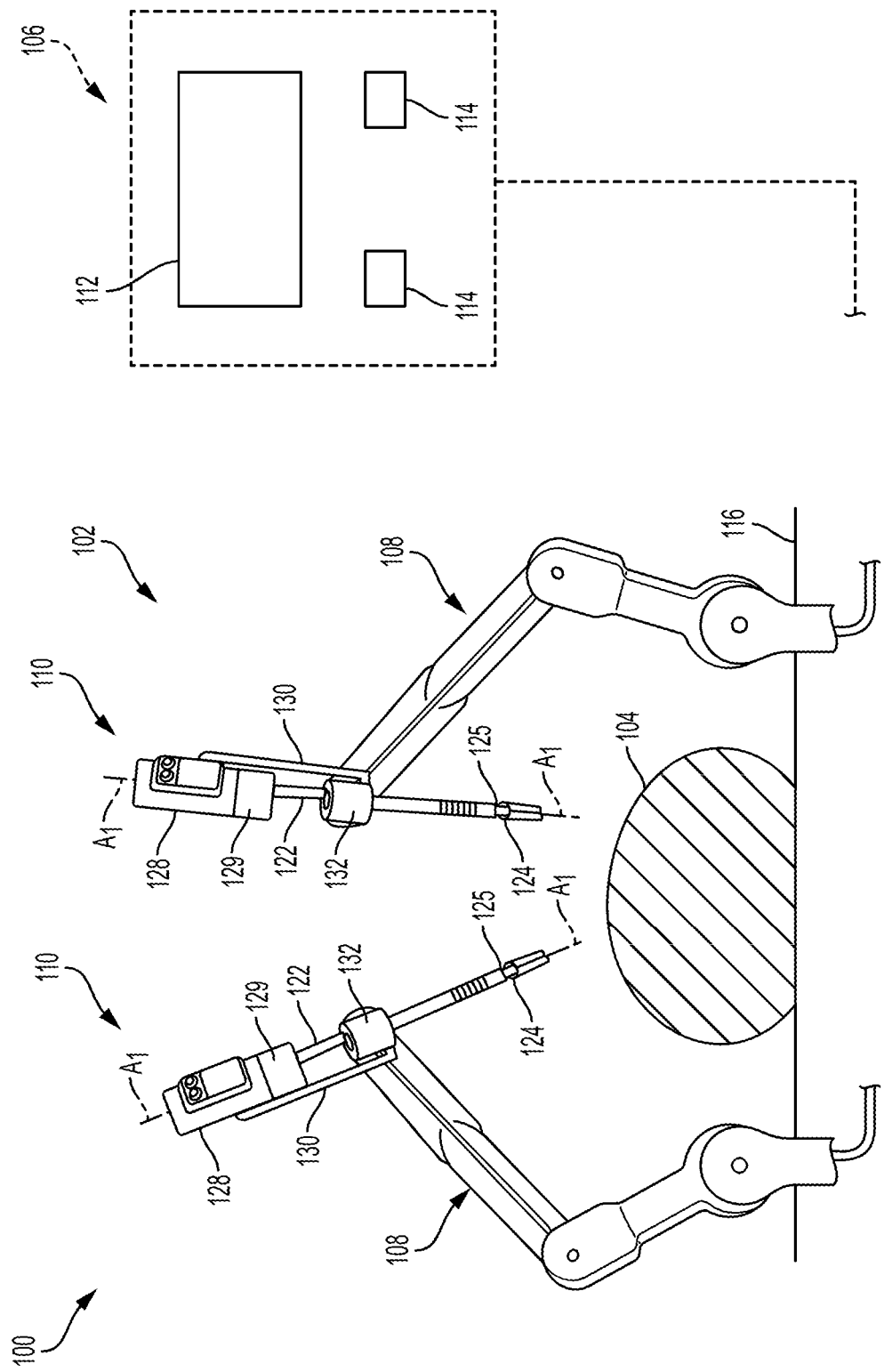
FIG. 1 is a perspective view of one embodiment of surgical robotic system that includes a patient-side portion and a user-side portion.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods, systems, and devices for initializing or resetting a surgical tool are provided. In particular, systems and methods for articulation calibration of surgical tools configured to be reversibly coupled to a robotic surgical system are provided. In general, a surgical tool can include an elongate shaft and a wrist that couples an end effector to a distal end of the shaft. The wrist can be configured to facilitate angular movement of the end effector relative to the shaft. The surgical tool can also include at least one linkage member operably coupled to the end effector such that force selectively applied to one or more of the linkage members is able to cause movement of the end effector relative to the shaft. The movement of the end effector can include movement between an unarticulated position that is taken to be a zero-angle position of the end effector and an articulated position, in which the end effector is moved relative to the zero-angle position and is orientated at a non-zero angle relative to the shaft. In at least some embodiments, the movement of the end effector is at least one of a pitch and a yaw motion of the end effector.

In at least some of the described embodiments, the surgical tool also includes a homing mechanism configured to be actuated to angularly adjust a presumed zero position of the end effector relative to the tool shaft to an adjusted zero position of the end effector. The homing mechanism is configured to substantially limit articulation of the end effector relative to the shaft. In some embodiments, additionally or alternatively, the end effector can be constrained such that its articulation is limited using other techniques. For example, the end effector can be at least partially inserted into a trocar or other instrument.

When the end effector is in the constrained configuration, articulation of the end effector can be calibrated. In one aspect the calibration involves applying force to the at least one linkage member to attempt articulation of the end effector until a resistance against further articulation exceeds a threshold. A force value at which the resistance exceeded the threshold is then used to determine an articulation angle of the end effector. The articulation attempts can be performed in a first direction and in a second, opposite direction, and respective determined articulation angles can be averaged. In this way, a home position of the end effector, at which an articulation angle of the end effector is taken to be a zero angle, is determined. The calibration can be performed each time the surgical tool is coupled to the robotic surgical system, to initialize or reset the tool. Subsequent operation of the surgical tool to articulate the end effector is performed with reference to the determined home position.

In particular, a first force can be applied to the at least one linkage member to attempt articulation of the end effector in a first direction until a resistance against further articulation exceeds a first threshold. In a similar manner, a second force can be applied to the at least one linkage member to attempt articulation of the end effector in a second, opposite direction until a resistance against further articulation exceeds a second threshold. This application of force is intended to remove mechanical hysteresis of each of the linkage members and determine tension of the linkage members at a home position of the end effector.

First and second values of a force at which the resistance has exceeded the first and second thresholds, respectively, is stored, and first and second articulation angles are determined based on the first and second values. For example, the surgical tool can store, in its memory, force values in association with respective articulation angles. Thus, a value of a force applied to the linkage member can be compared to the stored force values, and a matching value can be used to determine an articulation angle corresponding to the force value being queried.

The described techniques allow articulation of the end effector to be more precisely controlled since the initial position of the end effector is accurately determined. One or more actuators of the robotic surgical system (e.g., of a tool driver) can then control articulation of the end effector with respect to that initial position. Thus, when one or more of the linkage members are actuated to cause the end effector to articulate (e.g., pitch, yaw, or combination thereof), an amount of the movement can be more accurately determined to effect the desired direction and degree of articulation. The end effector may thus be more precisely positioned within a body of a patient in a surgical procedure and accordingly allow for more efficient performance of the surgical procedure and/or may reduce chances of the end effector moving to an unintended location and consequently damaging tissue and/or other matter. As another advantage, the calibration can be performed rapidly once the tool is coupled to the surgical system. Also, the surgical tool and components of the surgical system involved in the articulation calibration can be configured such that the calibration may not be perceptible by operating room staff.

FIG. 1 is a perspective view of one embodiment of a surgical robotic system 100 that includes a patient-side portion 102 that is positioned adjacent to a patient 104, and a user-side portion 106 that is located a distance from the patient, either in the same room and/or in a remote location. The patient-side portion 102 generally includes one or more robotic arms 108 and one or more surgical tools and/or tool assemblies 110 that are configured to releasably couple to a robotic arm 108. The user-side portion 106 generally includes a vision system 112 for viewing the patient 104 and/or surgical site, and a control system 114 for controlling the movement of the robotic arms 108 and each surgical tool 110 during a surgical procedure. A person skilled in the art will appreciate that the surgical robotic system can have a variety of configurations. One exemplary system is disclosed in WIPO Patent Publication No. WO2014/151621, filed on Mar. 13, 2014 and entitled "Hyperdexterous Surgical System," which is incorporated herein by reference in its entirety.

The patient-side portion 102 can have a variety of configurations. As illustrated in FIG. 1A the patient-side portion 102 is coupled to an operating table 116. However, in other embodiments, the patient-side portion 102 can be mounted to a wall, to the ceiling, to the floor, or to other operating room equipment. Further, while the patient-side portion 102 is shown as including two robotic arms 108, more or fewer robotic arms 108 may be included. Furthermore, the patient-side portion 102 can include separate robotic arms 108 mounted in various positions, such as relative to the surgical table 116 (as shown in FIG. 1A). Alternatively, the patient-side portion 102 can include a single assembly that includes one or more robotic arms 108 extending therefrom.

The surgical tool 110 includes an elongate shaft (also referred to herein as a "shaft" and a "tool shaft") 122, an end effector 124, a wrist 125 that couples the end effector 124 to the shaft 122 at a distal end of the shaft 122, and a tool housing 128 coupled to a proximal end of the shaft 122. The shaft 122 can have any of a variety of configurations. In general, the shaft 122 is an elongate member extending distally from the housing 128 and having at least one inner lumen extending therethrough. The shaft 122 is fixed to the housing 128, but in other embodiment the shaft 122 can be releasably coupled to the housing 128 such that the shaft 122 can be interchangeable with other shafts. This may allow a single housing 128 to be adaptable to various shafts having different end effectors.

The end effector 124 can also have a variety of sizes, shapes, and configurations. The end effector 124 can be configured to move relative to the shaft 122, e.g., by rotating and/or articulating, to position the end effector 124 at a desired location relative to a surgical site during use of the tool 110.

The wrist 125 can have any of a variety of configurations. Exemplary embodiments of a wrist of a surgical tool are described in International Patent Publication No. WO 2014/151952 entitled "Compact Robotic Wrist" filed on Mar. 13, 2014 and International Patent Publication No. WO 2014/151621 entitled "Hyperdexterous Surgical System" filed on Mar. 13, 2014, which are hereby incorporated by reference in their entireties. In general, the wrist 125 can include a joint configured to allow movement of the end effector 124 relative to the shaft 122, such as a pivot joint at which jaws of the end effector 124 are pivotally attached. In some embodiments, the pivoting motion can include pitch movement about a first axis of the wrist 125 (e.g., a X axis), yaw movement about a second axis of the wrist 125 (e.g., a Y axis), and combinations thereof to allow for 360° rotational movement of the end effector 124 about the wrist 125. In other embodiments, the pivoting motion can be limited to movement in a single plane, e.g., only pitch movement about the first axis of the wrist 125 or only yaw movement about the second axis of the wrist 125, such that end effector 124 rotates in a single plane.

The surgical tool 110 includes various other components. The housing 128 includes various components (e.g., gears and/or actuators) configured to control the operation of various features associated with the end effector 124 (e.g., any one or more of clamping, firing, rotation, articulation, energy delivery, etc.). The surgical tool 110 includes one or more linkage members (obscured in FIG. 1) configured to effect the movement of the end effector 124 relative to the shaft 122. The linkage members are operably coupled to the tool housing 128, extend within the shaft 122, extend at least partially through the wrist 125, and are operably coupled to the end effector 124. In an exemplary embodiment, the linkage members extend distally from the tool housing 128 along the shaft 122 within an inner lumen of the shaft 122.

The linkage members can be selectively actuated to cause the end effector 124 to pivot at the wrist 125 relative to the shaft 122. The selective actuation of the linkage members can cause any one or more of the linkage members to move, e.g., translate longitudinally, to cause the articulation. The one or more of the linkage members that translate depending on the requested articulation, e.g., to cause the end effector 124 to yaw and/or pitch as requested. The actuation can be accomplished in any of a variety of ways, such as by actuating an actuator operably coupled to the tool housing 128, as discussed further below. In general, the actuation applies force to the one or more of the linkage members in a proximal or distal direction to cause the one or more of the linkage members to translate and thereby cause the end effector 124 to articulate relative to the shaft 122. For example, the actuation can pull one or more of the linkage members proximally. The linkage members can also be selectively actuated to open and close the jaws of the end effector 14 between open and closed positions.

The linkage members can have any of a variety of configurations, for example cables, rods, wires, or twisted cables. The extended linkage members can include more than one component such that at least a portion of each linkage member can be flexible. The linkage members can be made from any of a variety of materials, such as a metal (e.g., Tungsten, stainless steel, etc.). Exemplary embodiments of flexible members of a surgical tool are described in previously mentioned International Patent Publication No. WO 2014/151952 entitled "Compact Robotic Wrist" filed on Mar. 13, 2014 and International Patent Publication No. WO 2014/151621 entitled "Hyperdexterous Surgical System" filed on Mar. 13, 2014.

Initialization or resetting of the surgical tool can result in a home position of the end effector 124 being established, as discussed below. The home position can be a position at which the end effector 124 is substantially longitudinally aligned with the shaft 122, e.g., a longitudinal axis of the end effector 124 is substantially aligned with the longitudinal axis A1 of the shaft 122 such that the end effector 124 is at a substantially zero angle relative to the shaft 122. However, in some embodiments, the home position can correspond to a position of the end effector at which it is angularly orientated relative to the shaft 122. The angular movement of the end effector 124 caused by movement of one or more of the linkage members includes movement of the end effector 124 between the home position and other non-zero angular positions of the end effector at which the end effector 124 is moved with respect to the home position and angularly orientated relative to the shaft 122.

The surgical tool 110 can include a homing mechanism configured to maintain the end effector 124 in a certain position. For example, the end effector 124 can be manipulated (manually by a user and/or in other ways) to move to a substantially unarticulated, zero-angle position. However, such an end effector position can be what is referred to herein as a perceived or presumed zero position. In other words, the end effector 124 can still be positioned at a slight angle (e.g., from about 1 degree to about 3 degrees, from about 1 degree to about 5 degrees, from about 5 to about 10 degrees, etc.) to the tool shaft 122. The homing mechanism can be activated to adjust the position of the end effector 124 relative to the shaft 122 to an adjusted zero position of the end effector 124. The adjusted zero position of the end effector corresponds to a smaller angle of the end effector 124 to the tool shaft 122 than an angle of the end effector 124 to the tool shaft 122 when the end effector 124 is in the perceived or presumed zero position. The adjusted zero position can be closer to the actual zero-angle position—for example, the end effector 124 can be positioned under a smaller (e.g., from about 0 degree to about 1 degree, from about 0 to about 3 degrees, etc.) angle to the tool shaft 122.

The homing mechanism is operably coupled between the end effector 124 and the tool housing 128 and extends along the shaft 122. In an exemplary embodiment, the homing mechanism includes one or more components configured to retain the end effector in a position desired for the tool initialization or resetting. In at least some embodiments, the homing mechanism is configured to be actuated to angularly adjust a presumed zero position of the end effector relative to the tool shaft to an adjusted zero position of the end effector. For example, for articulation calibration, an attempt can be made to bring into a substantially zero position (e.g., by being inserted into a trocar, manually manipulated, or manipulated in another way). This can be a presumed zero position which can, however, differ from an actual zero position (e.g., the end effector can be oriented under an angle with respect to the tool shaft). The homing mechanism is configured to adjust this presumed zero position to an adjusted zero position of the end effector, which can be a substantially zero position or another position of the end effector at which its oriented angularly with respect to the tool shaft. The tool can be calibrated with the end effector in the adjusted zero position.

The homing mechanism can have any suitable configuration. It can have one or more members that extend distally from the tool housing 128 along the shaft 122 within the shaft 122. The one or more members of the homing mechanism can be configured to be selectively actuated to force the end effector 124 into a substantial longitudinal alignment with the shaft 122 and/or to adjust a presumed zero position of the end effector 124. The actuation can be accomplished in any of a variety of ways, such as by actuating a suitable actuator operably coupled to the tool housing 128. In general, the actuation causes one or more components of the of the homing mechanism to move in a distal direction relative to the shaft 122 to engage the end effector 124, and a subsequent actuation causes the one or more components to move in a proximal direction and disengage from the end effector 124.

The tool housing 128 can have any of a variety of configurations. In general, the tool housing 128 can include one or more actuation mechanisms at least partially disposed therein configured to cause movement of the linkage members and thereby cause movement of the end effector 124 about the wrist 125. The one or more actuation mechanisms can include, for example, one or more movement mechanisms operably coupled to the linkage members, such as, e.g., pulley(s) configured to be moved to cause translation of the linkage members.

The tool housing 128 is configured to be releasably attached to a robotic surgical system (also referred to herein as a "surgical robot") so as to releasably attach the tool 110 to the surgical robot. The tool housing 128 can be configured to releasably attach to a robotic surgical system in any of a variety of ways, such as by clamping thereto, clipping thereto, or slidably mating therewith. The one or more movement mechanisms of the tool 110 are configured to be controlled by the surgical robot, such as by the surgical robot including one or more motors operably coupled to one or more inputs of the tool housing 128 that are operably coupled to the one or more movement mechanisms. In at least some embodiments, as in the illustrated embodiment of FIG. 1, the surgical tool 110 is configured to releasably couple to a tool driver 129 mounted on a carrier 130 on the distal end of the robotic arm 108. The tool housing 128 can include coupling features configured to allow the releasable coupling of the tool 110 to the tool driver 129. The carrier 130 can also include a trocar support or a trocar 132 mounted on a distal end thereof and configured to receive a shaft 122 of the tool 110 therethrough.

The robotic surgical system includes a computer system that can receive user inputs and that can control the motor(s) in response to the user inputs and hence control movement of the flexible members and consequently the end effector 124. The one or more inputs of the tool housing 128 are also operably coupled to the one or more homing members to allow the robot to control movement of the one or more homing members. A person skilled in the art will appreciate that the surgical tool 110 can have any of a variety of configurations, and it can be configured to perform at least one surgical function. The surgical tool can be, for example, a stapler, a clip applier, forceps, a grasper, a needle driver, scissors, an electrocautery tool that applies energy, a suction tool, an irrigation tool, an imaging device (e.g., an endoscope or ultrasonic probe), etc.

The control system 114 can have a variety of configurations and can be located adjacent to the patient (e.g., in the operating room), remote from the patient (e.g., in a separate control room), or distributed at two or more locations operating room and/or separate control room(s)). As an example of a distributed system, a dedicated system control console can be located in the operating room, and a separate console can be located in a remote location. The control system 114 can include components that enable a user to view a surgical site of the patient 104 being operated on by the patient-side portion 102 and/or to control one or more parts of the patient-side portion 102 (e.g., to perform a surgical procedure at the surgical site). In some embodiments, the control system 114 can also include one or more manually-operated input devices, such as a joystick, exoskeletal glove, a powered and gravity-compensated manipulator, or the like. The one or more input devices can control teleoperated motors which, in turn, control the movement of the surgical system, including the robotic arms 108 and surgical tools 110.

Figure 2:
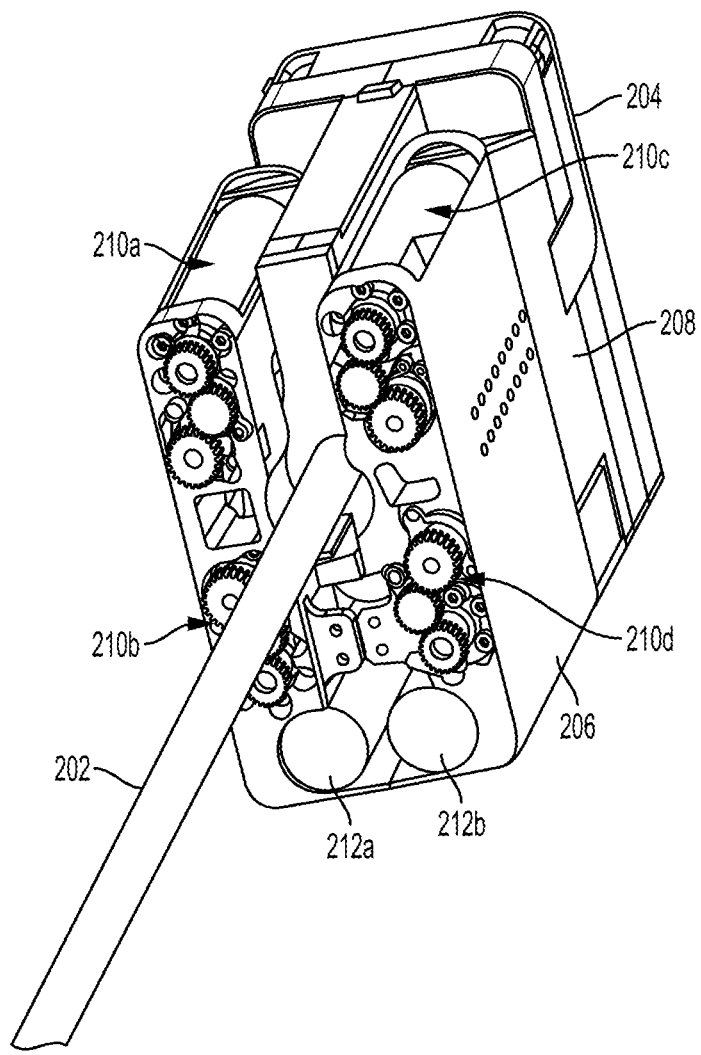
FIG. 2 is a perspective view of a tool driver of a surgical robotic system and a proximal portion of a surgical tool coupled to the tool driver.

A surgical tool which can be calibrated using the techniques described herein can be releasably coupled to one embodiment of a robotic surgical system. FIG. 2 illustrates a tool 200 having a tool housing 204 is releasably coupled to a tool driver 206 of the robotic surgical system with the shaft 202 of the tool 200 extending distally from the tool housing 204 and the tool driver 206. Only a partial portion of the robotic surgical system is shown in FIG. 2 for clarity of illustration. In this example, the robotic surgical system also includes a sterile barrier 208 to which a sterile shroud or drape (not shown) can be attached for sterility purposes, though in some embodiments the sterile barrier can have another configuration and it can be absent. The placement of the sterile barrier 208 between the tool housing 204 and the tool driver 206 may ensure a sterile coupling point for the tool 200 and the robot and thereby permit removal the tool 200 from the robot to exchange with other surgical tools during the course of a surgery without compromising the sterile surgical field.

The tool driver 206 can have any of a variety of configurations. In the illustrated implementation, the tool driver 206 includes one or more motors for controlling a variety of movements and actions associated with tools such as the tool 200 that can be releasably coupled to the tool driver 206, as will be appreciated by a person skilled in the art. In this illustrated embodiment, the tool driver 206 includes six motors, four motors 210a, 210b, 210c, 210d for driving movement/action using activation features and one motor 212a, 212b for each of two rotary couplings of the tool driver 206 for driving movement/action through rotary motion. For example, each motor 210a, 210b, 210c, 210d, 212a, 212b can couple to and/or interact with an activation feature (e.g., gear) associated with the tool 200 for controlling one or more actions and movements that can be performed by the tool 200, such as movement of the tool's linkage members relative to the shaft 202, movement of the tool's homing mechanism relative to the shaft 202, articulation of the tool's end effector, rotation of the shaft 202 about its longitudinal axis, etc.

The movement of the linkage members (e.g., pulling thereof in a proximal direction or pushing in a distal direction) can be independently controlled by their associated motors 210a, 210b, 210c, 210d. Rotary motion of the motors 210a, 210b, 210c, 210d can thus be configured to cause translational movement of the linkage members. One of the motors 212a, 212b can be configured to cause translational movement of the homing mechanism. In another embodiment, one of the motors 210a, 210b, 210c, 210d is operably coupled to the tool's homing mechanism.

The motors 210a, 210b, 210c, 210d, 212a, 212b are accessible to the tool housing 204 of the tool 200 that can be configured to mount on a proximal end of the sterile barrier 208 to couple to the sterile barrier 208 and the tool driver 206. Exemplary embodiments of motors and movements and actions motors can drive are described in previously mentioned International Patent Publication No. WO 2014/151952 entitled "Compact Robotic Wrist" filed on Mar. 13, 2014 and International Patent Publication No. WO 2014/151621 entitled "Hyperdexterous Surgical System" filed on Mar. 13, 2014.

The tool housing 204 includes features configured to assist with releasably coupling the tool housing 204 to the tool driver 206, and hence for coupling the tool 200 to the robotic surgical system. Thus, the tool housing 204 includes gears and/or actuators configured to be actuated by one or more of the motors 210a, 210b, 210c, 210d, 212a, 212b. The gears and/or actuators in the tool housing 204 can control the operation of various features associated with the tool's end effector (e.g., clamping, articulation, firing, rotation, energy delivery, forcing to an unarticulated position, etc.), as well as control the movement of the shaft 202 (e.g., rotation of the shaft). The shaft 202 can include actuators and connectors that are operably coupled to the gears and/or actuators in the tool housing 204 and that extend along the shaft 202 to assist with controlling the actuation and/or movement of the end effector and/or the shaft 202. Each motor on the surgical system can be associated with one or more sensors or other components facilitating control of operation of one or more actuators. A suitable controller can control the motors to operate (e.g., rotate) to translate linkage members to effect the desired articulation of the end effector. The rotation of the motor can be generally proportional to a desired articulation angle of the end effector.

In the described embodiments, an end effector of a surgical tool, coupled to a distal end of a tool shaft, can be calibrated at tool initialization or resetting. The calibration involves determining a position (i.e. angle) of the end effector with respect to the shaft each time the tool is coupled to a suitable component of robotic surgical system. In particular, a home position of the end effector can be determined, which indicates a position of the end effector at which an articulation angle of the end effector with respect to the shaft is considered to be zero.

Figure 3:
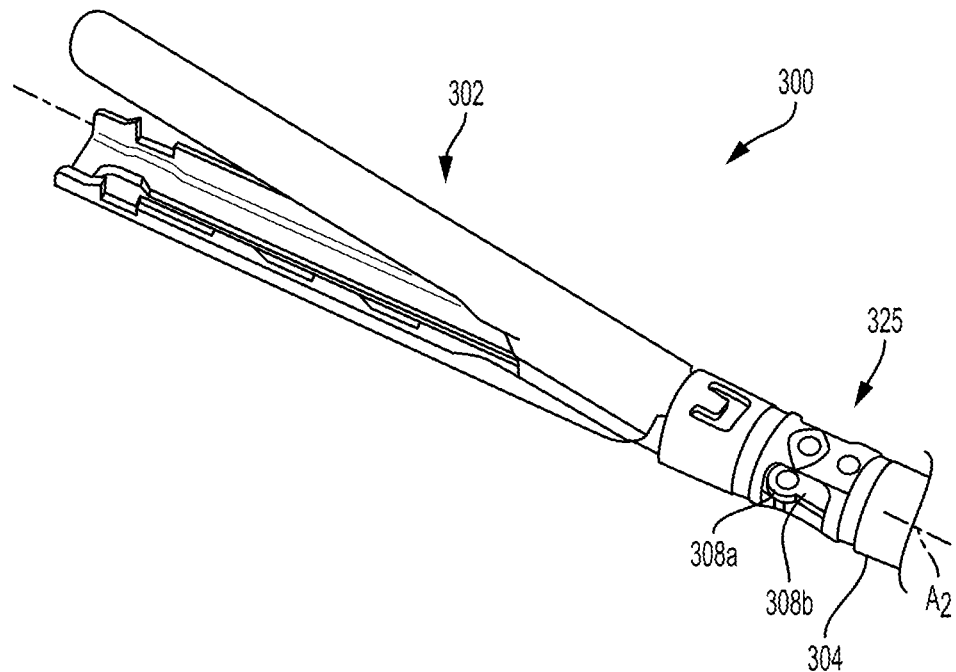
FIG. 3 is a perspective view of an end effector and a wrist of a surgical tool.
Figure 4:
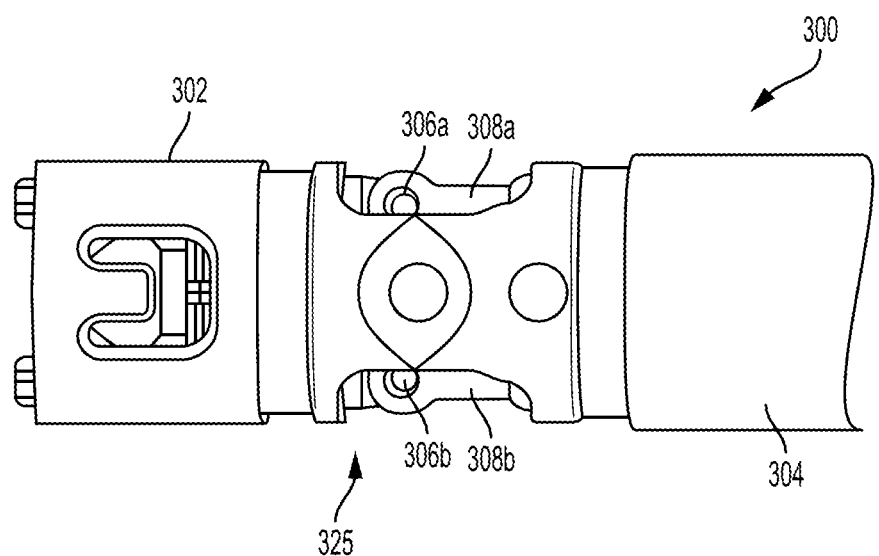
FIG. 4 is another perspective view of the wrist of FIG. 3.

The articulation joint or wrist, such as, e.g., wrist 125 in FIG. 1, can have a variety of configurations. FIGS. 3 and 4 illustrate an embodiment of a surgical tool 300 (shown partially) including an articulation joint or wrist 345 disposed between an end effector 302 and a shaft 304 of the surgical tool 300. The wrist 345 is configured to allow the end effector 302 to form a variety of angles relative to a longitudinal axis A2 of the elongate shaft 304. The wrist 325 can include first and second pivot points 306a, 306b, respectively, that are coupled to first and second elongate linkage members 308a, 308b, respectively. The linkage members 308a, 308b extend through and along the shaft 304 and at least partially through the wrist 345, as shown in FIGS. 3 and 4.

Each of the linkage members 308a, 308b is operably coupled to the end effector 302 such that force selectively applied to the linkage member causes at least one of a pitch and a yaw motion of the end effector 302. For example, translation of the first linkage member 308a and the first pivot point 306a in a distal direction can cause the end effector 302 to pivot in a first direction about both the first and second pivot points 306a, 306b. Translation of the second linkage member 308b and second pivot point 306b in the distal direction can cause the end effector 301 to pivot about both the first and second pivot points 306a, 306b in a second direction. The first and second directions can be in opposite directions from each other.

Figure 5:
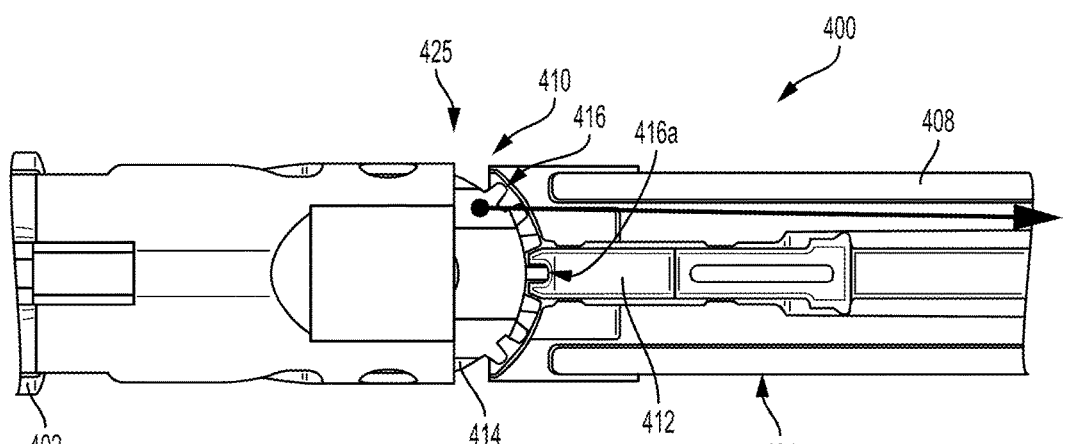
FIG. 5 is a perspective view of a homing mechanism of a surgical tool configured to be removably coupled to a surgical robotic system.

FIG. 5 illustrates an embodiment of a surgical tool 400 including a tool shaft 404 having an end effector 402 coupled to a distal end thereof, and a wrist 425 disposed between the tool shaft 404 and the end effector 402. As shown in FIG. 5, the surgical tool 400 also includes at least one linkage member 408 extending along the shaft 404 and operably coupled to the end effector 402 such that force selectively applied to the linkage member is able to cause at least one of a pitch and a yaw motion of the end effector 402. One linkage member 408 is shown in FIG. 5, though a surgical tool implementing the described techniques can include two or more linkage members. The linkage member 408 is an elongate element that extends between the end effector 402 and an actuator of robotic surgical system. For example, the linkage member 408 can be operably coupled to an actuator disposed in a tool driver of the robotic surgical system and configured to effect movement of the linkage member 408 to thus control movement of the end effector 402. The linkage member 408 can include one or more flexible cables, though one or more components of the linkage member 408 can be rigid.

As shown in FIG. 5, the tool 400 also includes a homing mechanism 410 configured to be actuated to angularly adjust a presumed zero position of the end effector 402 relative to the shaft 404 to an adjusted zero position of the end effector 402. In this embodiment, the homing mechanism 410 includes an elongate element 412 and an engagement member 414 associated with the wrist 425. The elongate element 412 can be in the form of a rod that extends through the shaft 404 of the tool 400 and is operably coupled to and driven by an appropriate actuator disposed, e.g., on a tool driver of the robotic surgical system. The engagement member 414 is part of the wrist 425 and is configured to allow movement of the end effector 402 with respect to the shaft 404.

In the illustrated example, the elongate element 412 is configured to move distally to engage the engagement member 414. As shown in FIG. 5, the engagement member 414 can be at least partially cylindrical and it can have a plurality of teeth 416. In use, the end effector 402 can be constrained (e.g., inserted into a trocar and/or manually constrained) such that it is angularly adjusted to adopt a presumed zero position. As mentioned above, the presumed zero position is a position of the end effector 402 that is close to a zero angle position, but at which the end effector 402 can be disposed at an angle relative to the shaft 404.

The elongate element 412 is then actuated to be moved distally and engage the engagement member 414. In particular, in this example, the elongate element 412 engages at least one of the teeth 416. FIG. 5 shows that a distal end 412a of the elongate element 412 engages a tooth 416a of the teeth 416 of the engagement member 414. In some embodiments, however, the engagement member 414 may not have any teeth or other mating features, such that the elongate element 412 can be configured to be frictionally engaged with the engagement member 414.

Regardless of the specific way in which the elongate element 412 engage the engagement member 414 when the elongate element 412 moves distally, the engagement causes articulation of the end effector 402 relative to the shaft 404 to be substantially limited. The engagement between the elongate element 412 and the tooth 416a, as in the example shown in FIG. 5, causes the presumed zero position of the end effector 402 relative to the tool shaft 404 to be adjusted to an adjusted zero position of the end effector 402. In other words, as the elongate element 412 is brought into contact with the engagement member 414, the elongate element 412 engages the tooth 416a and is thus displaced slightly such that it "adjusts" the angular orientation of the end effector 402 relative to the shaft 404. The end effector 402 thus becomes constrained relative to the shaft 404. The calibration of the end effector 402 in such constrained configuration can then be performed.

Figure 6:
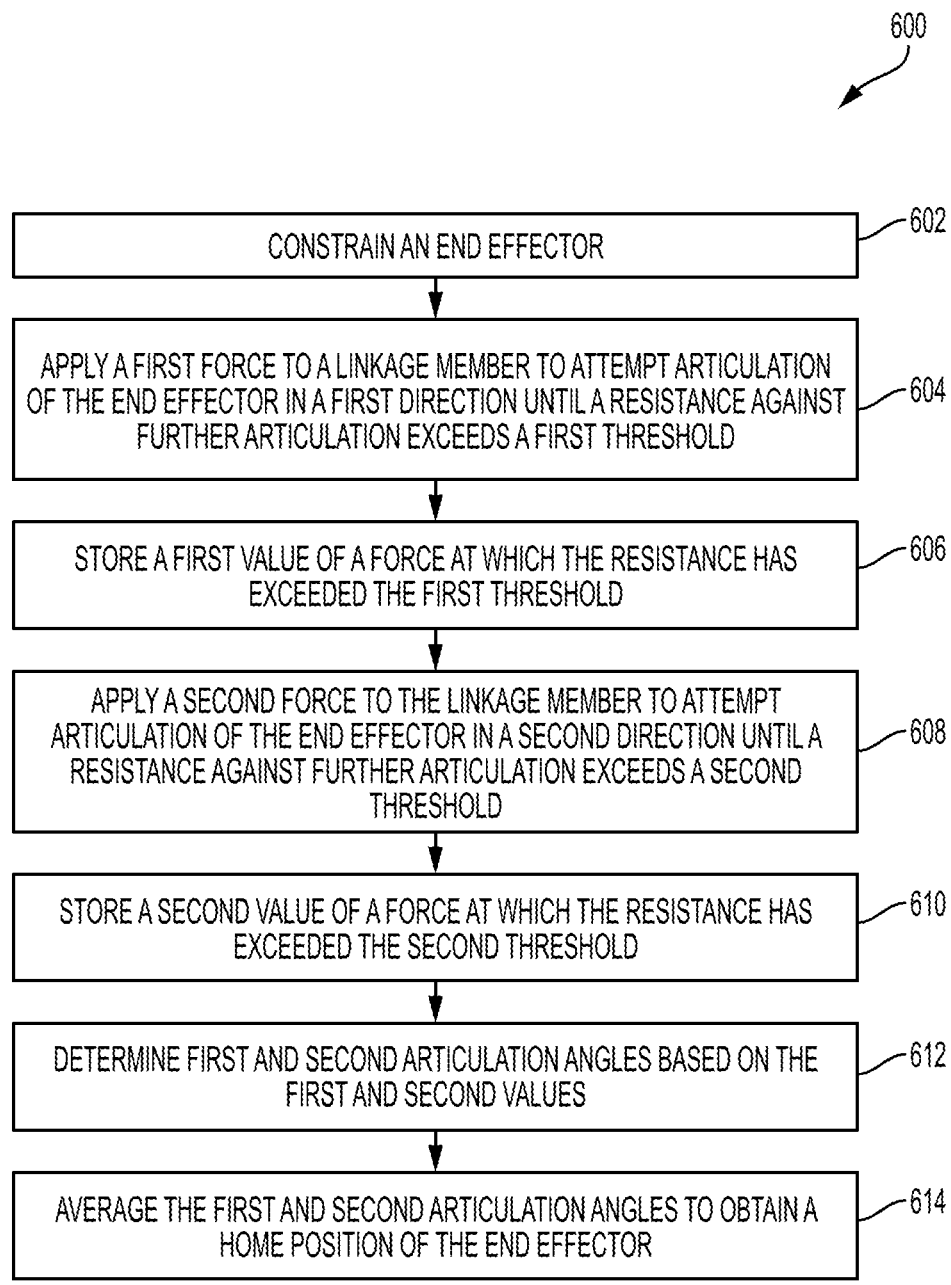
FIG. 6 is a flowchart of a process of articulation calibration of an end effector of a surgical tool configured to be removably coupled to a surgical robotic system.

It should be appreciated that FIG. 5 illustrates the homing mechanism 410 by way of example only. An end effector coupled to a distal end of a shaft of a surgical tool can be constrained in various ways such that its articulation relative to the shaft is substantially limited. The surgical tool can include one or more linkage members. FIG. 6 illustrates generally a surgical method 600 that can be performed to calibrate articulation of the end effector. The method 600 can be performed to calibrate tool 300 (FIGS. 3 and 4), tool 400 (FIG. 5), or any other tool. The method 600 can be performed when the surgical tool is installed on the robotic surgical system for the first time. Also, the method 600 can be performed during a surgical procedure, after the tool has been removed from the robotic system and then re-connected with the system. In either of these situations, it is useful to determine an initial articulation angle of the end effector which can be defined as a home position of the end effector. Once the home position is determined, the tool can be operated so as to effect articulation of the end effector in a controlled manner.

As shown in FIG. 6, the end effector can be constrained at block 602, to substantially limit articulation of the end effector relative to the shaft. For example, as discussed above in connection with FIG. 5, constraining the end effector can involve actuating a homing mechanism member to substantially limit articulation of the end effector relative to the shaft. Other mechanisms can be used to limit movements of the end effector, as discussed below. The end effector can also be constrained by being at least partially inserted into a trocar, as discussed below, or in other suitable ways.

At block 604, a first force can be applied to at least one linkage member operably coupled to the end effector to attempt articulation of the end effector in a first direction until a resistance against further articulation exceeds a first threshold. For example, with reference to FIG. 5, an actuator of a robotic surgical system (not shown) can be activated to cause a force to be applied to the linkage member 408 in the locked configuration, to attempt articulation of the end effector 402 in a first direction. The force can be applied to attempt articulation of the end effector 402 (which is held in the constrained configuration) to the left, until resistance against further articulation exceeds a first threshold. The first threshold can define a state of the actuator at which actuator stabilization is achieved, and non-limiting examples of it can include a force or a change in a force applied by the actuator, a velocity of the actuator, etc. A first value of a force at which the resistance has exceeded the first threshold can be stored at block 606.

At block 608, a second force can be applied to the at least one linkage member to attempt articulation of the end effector in a second, opposite direction until a resistance against further articulation exceeds a second threshold. For example, with reference to FIG. 5, an actuator of the robotic surgical system can be activated to cause a force to be applied to the linkage member 408 to attempt articulation of the end effector 402 to the right. When the end effector has one linkage member, as in the example of FIG. 5, the linkage member can be translated proximally to attempt articulation of the end effector in one of the first and second directions, and distally to attempt articulation of the end effector in the opposite direction. However, in embodiments in which the surgical tool includes two or more linkage members, one of the linkage members can be configured to be translated proximally to attempt articulation of the end effector in a first direction, and another linkage members can also be configured to be translated proximally to attempt articulation of the end effector in a second, opposite direction.

Thus, regardless of the number of linkage members, attempts are made to articulate the end effector in two opposed directions while it is maintained in the constrained configuration. The linkage member can be pulled or pushed until a predetermined threshold is reached. This establishes a torque applied to the linkage members to bring the end effector to a zero positon. This torque is determined and then used by actuators configured to cause the linkage members to translate. For example, in at least one embodiment, the force can be 2-10 pounds or 0-3 pounds. In other words, with the end effector in the constrained configuration, a force is applied to the linkage member, which is at least partially flexible (i.e. at least one of its components is flexible) to at both directions. The force is applied until a certain value is sensed by the actuator (or a suitable sensor associated therewith).

Figure 12:
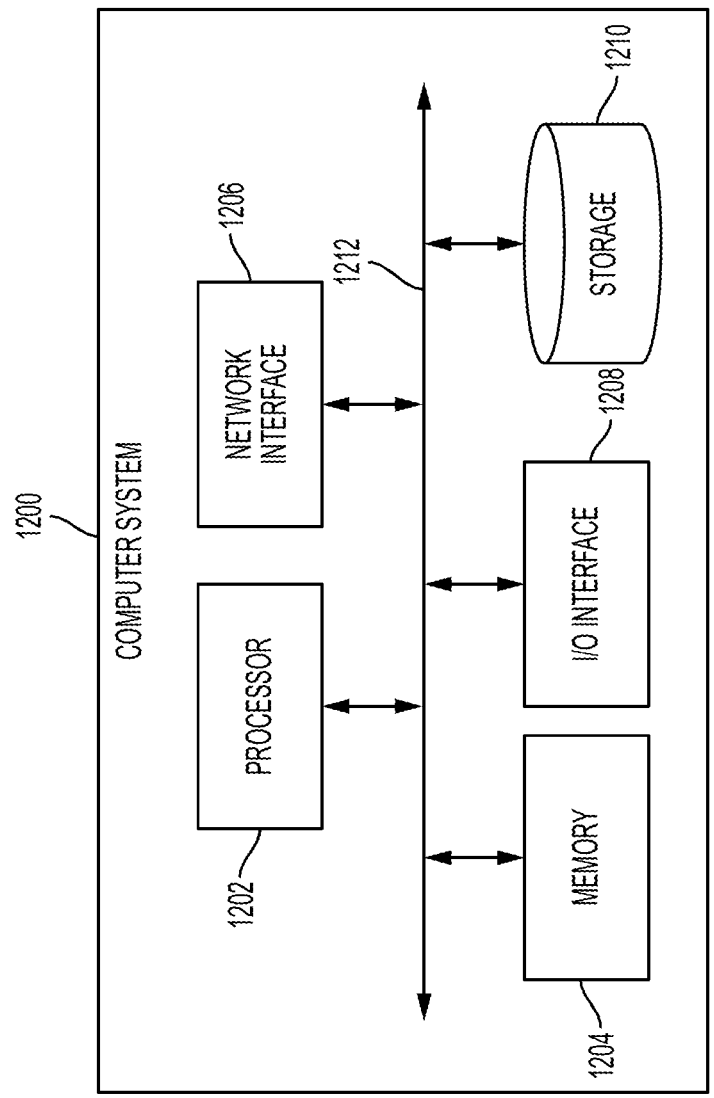
FIG. 12 is a block diagram illustrating a computing system.

Referring back to FIG. 6, similar to the first value of the force at which the resistance has exceeded the first threshold, a second value of a force at which the resistance has exceeded the second threshold can be stored at block 610. The first and second values can be stored in a volatile or a non-volatile memory unit associated with the robotic surgical system. For example, these values can be stored in memory of a computing device of the robotic surgical system, as example of which is shown in FIG. 12 below.

Figure 7:
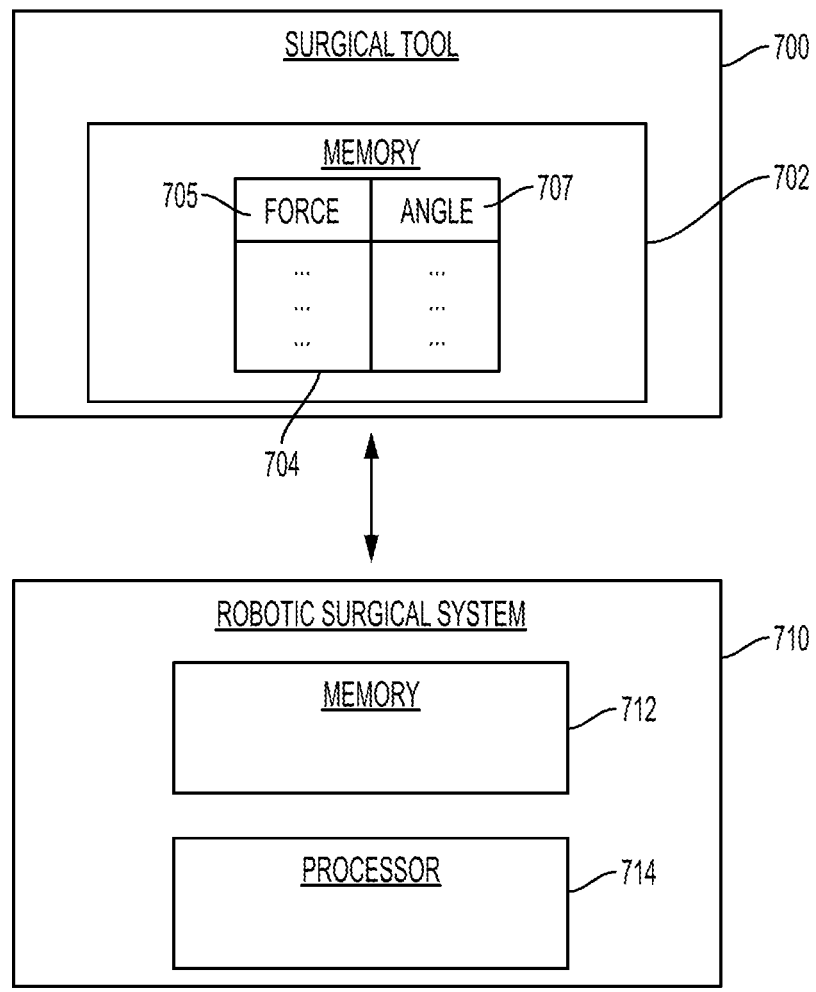
FIG. 7 is a block diagram illustrating a surgical tool and a surgical robotic system.

The first and second values can be used to determine first and second articulation angles of the end effector, at block 612 of FIG. 6. This involves correlating the first and second values with stored values of a force that can be applied to the at least one linkage member, each of the stored values being stored in association with a respective value of an articulation angle. For example, FIG. 7 illustrates schematically that a surgical tool 700 can have a memory unit or memory 702 storing in a suitable data structure 704 force values ("Force") 705 that can be applied to at least one linkage member, in association with respective values ("Angle") 707 of an articulation angle. The data structure 704 can be a database or other suitable data structure. The force values 705 and corresponding articulation angle values 707 can be stored in the memory 702 during manufacturing and/or assembly of the surgical tool 700. In some embodiments, the force values and articulation angle values 705, 707 can be stored for each linkage member extending through a shaft of the tool 700. In other embodiments, however, the same stored values can be applicable to all linkage members.

The surgical tool 700 shown schematically in FIG. 7 can be coupled to a robotic surgical system 710, also shown schematically in FIG. 7. The robotic surgical system 710 can include a memory unit or memory 712 and at least one processor 714. The memory unit 712 and the processor 714 can be included in a suitable computing device that can be part of the robotic surgical system 710 or that can be a remote computing device configured to communicate with the robotic surgical system 710. It should be appreciated that the robotic surgical system 710 includes various other components that are not shown in FIG. 7 for the sake of clarity.

The memory 712 can be any suitable computer readable medium configured to store computer-executable instructions. The memory 712 is configured to be accessed by the at least one processor 714 that is configured to execute the computer-executable instructions to perform various functions. The memory 712 can also store the first and second thresholds, which can be any suitable predetermined values. The first and second thresholds, which can have the same or different values, can be selected based on properties of the respective actuators configured to effect movement of linkage members operably coupled thereto, and/or based on the properties and configuration of the linkage members. It should be appreciated that the memory 712 can store more than two thresholds, such that articulation calibration of a tool having more than one linkage can be performed. Additionally or alternatively, in some instances, the thresholds can be stored in memory of the tool 700.

In the illustrated embodiments, during the articulation calibration of the surgical tool 700, the memory 712 can store the measured first and second values of the force at which the resistance has exceeded the first and second thresholds, respectively. To determine the first and second articulation angles, the processor 714 of the robotic surgical system 710 accesses the tool memory 702 to obtain the force values and articulation angle values 705, 707 stored in the memory 702. Each of the measured first and second values of the force at which the resistance has exceeded the first and second thresholds can be correlated (e.g., using the processor 714) with the force values 705. In particular, the measured first and second values are compared with the stored force values 705 to identify a matching force value among the force values 705. The value of the articulation angle 707 corresponding to the matching force value is the determined articulation angle. In this way, both the first and second articulation angles are determined. As mentioned above, the tool memory 702 can store force values and corresponding articulation angle values for more than one linkage member. In some instances, different force values and respective articulation angle values can be stored for different linkage members. Thus, in such instances, different values can be retrieved from the tool memory 702, depending on the linkage member to which the force was applied during the calibration or resetting.

Referring back to FIG. 6, after the first and second articulation angles are determined, their values can be averaged at block 614 (using, e.g., the processor 714) to obtain a home position of the end effector. The home position indicates a position of the end effector at which an articulation angle of the end effector with respect to the shaft is considered to be zero. Thus, during operation of the surgical tool which is thus calibrated, a force is applied to the at least one linkage member to cause at least a portion of the end effector to pivot relative to the shaft with reference to the home position of the end effector. In other words, subsequent articulation of the end effector is effected with respect to the home position. The home position allows control of the operation of actuators on the surgical system so as to translate the linkages to cause end effector articulation with respect to a known position of the actuators. The system is aware of a rotary input position and it gets informed about an actual articulation angle.

FIG. 5, discussed above, illustrates an example of a homing mechanism. As mentioned above, different homing mechanisms can be used to adjust a presumed zero position of the end effector relative to the tool shaft to an adjusted zero position of the end effector. Thus, FIGS. 8A and 8B illustrate another embodiment of a homing mechanism 810 of a surgical tool 800. The surgical tool 800 has a wrist 825 disposed between an end effector 802 and a shaft 80, and the homing mechanism 810 extend at least in part through the shaft 804. The tool 800 includes first and second linkage members 808a, 808b coupled to the wrist 825 via pins 809a, 809b, respectively. In this implementation, each of the first and second linkage members 808a, 808b has a portion along a length thereof that has first and second teeth 811a, 811b facing each other, as shown in FIG. 8A.

In this example, as shown in FIGS. 8A and 8B, the homing mechanism 810 includes an expandable fork member 814 and an elongate push rod 812 that is configured to move distally to engage with the fork member 814 to thereby lockingly engage the linkage members 808a, 808b, as discussed in more detail below. The push rod 812 extends through the shaft 804 of the tool 800 and is coupled to and driven by an appropriate actuator disposed, e.g., on a tool driver of the robotic surgical system. The fork member 814 includes a distal body 816 and first and second arms 818a, 818b extending proximally therefrom, as shown in FIG. 8B. As also shown in FIG. 8B, the fork member 814 has first and second teeth 820a, 820b disposed on the outer surface of the fork member 814, along at least a portion of the body 816 and each of the first and second arms 818a, 818b.

The push rod 812 of the homing mechanism 810 is coupled to and configured to be driven by a suitable actuator disposed, e.g., in a tool driver of a robotic surgical system to which the tool 800 is configured to be removably coupled. In use, as shown in FIG. 8B, the push rod 812 is configured to be moved distally into the fork member 814 such that the push rod 812 is disposed at least partially between the first and second arms 818a, 818b, along at least a portion of the arms 818a, 818b. In at least one embodiment, the push rod 812 is configured to always be disposed between the arms 818a, 818b, such that in use the push rod 812 is caused to move further distally towards the body 816 of the fork 814.

Regardless of its original position, in use, the push rod 812 is configured to be moved distally into the fork member 814 to thereby cause the fork member 814 to lockingly engage the linkage members 808a, 808b. Thus, as in the example illustrated, when the push rod 812 is driven distally between the arms 818a, 818b of the fork 814, the arms 818a, 818b move slightly apart such that the fork 814 can be said to expand. The push rod 812 can cause the arms 818a, 818b of the fork 814 to be brought closer to the linkage members 808a, 808b, such that the first and second teeth 820a, 820b formed on the arms 818a, 818b engage the first and second teeth 811a, 811b formed on the linkage members 808a, 808b, as shown in FIGS. 8A and 8B. Different sections of the teeth 820a, 820b formed on the arms 818a, 818b can engage different sections of the teeth 811a, 811b of the linkage members 808a, 808b.

Regardless of the specific way in which the teeth 820a, 820b engage with teeth 811a, 811b, the engagement allows adjusting a presumed zero position of the end effector 802 relative to the tool shaft 804 to an adjusted zero position of the end effector. Thus, the end effector 802 can be constrained to substantially limit its articulation relative to the shaft 804. With the end effector 802 constrained in this manner, articulation of the end effector 802 can be calibrated as discussed above. After the calibration is complete, the push rod 812 can be retracted proximally to allow the fork's teeth 820a, 820b to disengage from the teeth 811a, 811b of the linkage members 808a, 808b.

FIGS. 9A and 9B illustrate that, additionally or alternatively to using a homing mechanism, an end effector of a surgical tool can be constrained by being inserted into a trocar or other similar feature. In this example, an end effector 902 coupled distally to a shaft 902 of a surgical tool 900 is shown. The tool 900 includes first and second linkage members 908a, 908b extending along the tool shaft 904 and operably coupled to the end effector 902 such that force selectively applied to each linkage member is able to cause at least one of a pitch and a yaw motion of the end effector 902.

In the illustrated implementation, the end effector 902, which can be similar to the end effector 802 in FIGS. 8A and 8B, can be constrained by being inserted into a trocar 905, as shown schematically in FIGS. 9A and 9B. The trocar 905 can be similar, for example, to trocar 132 shown in FIG. 1, through the trocar 905 can have any suitable configuration. An inner diameter of the trocar 905 can be such that an articulation angle of the end effector 902 can be limited to about 10 degrees or less in both directions (clockwise and counterclockwise), or to about 5 or less degrees in both directions. For example, the inner diameter of the trocar 905 can be only slightly greater than an outer diameter of the end effector 902.

In this example, once the end effector 902 is constrained using the trocar 905, articulation calibration of the end effector 902 can be performed. Such calibration can be performed, for example, as discussed above in connection with FIGS. 6 and 7. In this way, a force can be applied to each of the linkage members 908a, 908b to attempt articulation of the end effector 902 in a selected direction until a resistance against further articulation exceeds a threshold. The linkage members 908a, 908b can be configured to be translated distally or proximally to effect articulation of the end effector 902. During calibration, the force can be applied until the end effector 902 hits the inner wall 907 of the trocar 905 as the end effector 902 is being articulated due to translation of one of the linkage members 908a, 908b. Thus, rather than using a predetermined value of a threshold, during articulation calibration, the end effector 902 can be articulated until it is not feasible to move it any further. However, in some embodiments, an appropriate force threshold can be used. For example, after the end effector 902 encounters the inner wall of the trocar 905 as the force is being applied to the end effector 902, the force can be further applied to the end effector 902, until a resistance against further articulation exceeds that threshold.

Regardless of the mechanism or feature that is used to constrain the end effector, a home position of the end effector can be determined as discussed above. Position of the linkage members at the home position of the end effector is provided to one or more actuators of the system that, in use, can control articulation of the end effector with respect to the home position —i.e. with respect to the force that needs to be applied to the linkages and torque of the actuators. FIGS. 10A and 10B illustrate a portion of a surgical tool 1000 including a shaft 1004, an end effector 1002 coupled distally to the shaft 1004, and a wrist 1025 disposed between the end effector 1002 and the shaft 1004. As shown, the tool 1000 includes first and second linkage members 1008a, 1008b extending along the tool shaft 1004 and operably coupled to the end effector 1002 such that force selectively applied to each linkage member 1008a, 1008b is able to cause at least one of a pitch and a yaw motion of the end effector 1002. The tool 1000 can have a homing mechanism similar, e.g., to homing mechanism 810 in FIGS. 8A and 8B. Also, although not shown in FIGS. 10A and 10B, the tool 1000 can also be inserted into a trocar.

FIGS. 10A and 10B illustrate schematically that, after a homing position of the end effector 1002 has been determined (which can be done in a manner described above), the linkage members 1008a, 1008b can be translated distally or proximally, as shown by bidirectional arrows 1013a, 1013b, respectively. These are the movements initiated by a user (e.g., a surgeon) or by the surgical system during the use of the calibrated tool 1000. For example, during articulation of the calibrated tool 1000, the linkage members 1008a, 1008b can be translated in the same direction to enable an antagonistic control method. Conversely, during firing of the calibrated tool 1000, the linkage members 1008a, 1008b can be translated in opposing directions to enable a cooperative control method.

FIGS. 11A and 11B illustrate a homing mechanism 1110 of a surgical tool 1100 that is similar to homing mechanism 810 shown in FIGS. 8A and 8B. Thus, the homing mechanism 1110 includes a push rod 1112 and an expandable fork member or fork 1114. The surgical tool 1100 includes a shaft 1104 and an end effector 1102 coupled to a distal end thereof, with a wrist 1125 being coupled between the end effector 1102 and the shaft 1104. The push rod 1112 is configured to move distally into the fork 1114 to cause the fork 1114 to expand and thereby lockingly engage linkage members 1108a, 1108b. As shown, the fork 1114 has a plurality of teeth 1120a, 1120b disposed on its first and second arms 1118a, 1118b. The teeth 1120a, 1120b are configured to engage a plurality of teeth 1111a, 1111b formed on the linkage members 1108a, 1108b.

In this example, the homing mechanism 1110 is configured to angularly adjust a presumed zero position of the end effector 1102 by causing the teeth 1120a, 1120b of the fork 1114 to engage the teeth 1111a, 1111b formed on the linkage members 1108a, 1108b such that the linkage members become disposed at one of a plurality of predetermined positions with respect to the homing mechanism 1110. In particular, the teeth 1111a, 1111b and 1120a, 1120b are configured such that, as the end effector 1102 is moved from the presumed zero position to an adjusted zero position, the teeth "jump" to the adjusted zero position. The teeth formed on the linkage members and on the fork 1114 can be configured to be releasably locked at a number of discrete positions. In this way, when, during calibration, the end effector 1102 is caused to be disposed at a certain angle with respect to the shaft 1104 (e.g., manually, by being inserted into a trocar, or in other way(s)), the teeth are automatically moved to be engaged into one of the discrete positions. This can be taken as an adjusted zero position of the end effector. In some implementations, the teeth can be locked in such a position using locking features 1122a, 1122b shown schematically in FIG. 11B.

Regardless of the way in which the teeth 1111a, 1111b and 1120a, 1120b engage at one of predetermined positions, the end effector 1102 becomes constrained at a certain angle. During calibration, a force is applied to the linkage members 1108a, 1108b, as schematically shown by arrow 1130 in FIG. 11A for the linkage member 1108b. It should be appreciated that, although the arrow 1130 illustrates that the linkage member 1108b can be pulled proximally, in some implementations, one or more of linkage members of an end effector can be pushed distally. As discussed above, the force is applied to attempt articulation of the end effector 1102 in first and second directions until a resistance against further articulation exceeds first and second thresholds, respectively. Further processing can be performed as described above. Once the end effector 1102 is calibrated and its home position is determined similar to the manner described above, the end effector 1102 can be used in a surgical procedure as desired.

FIG. 12 illustrates one exemplary embodiment of a computer system 1200. As shown, the computer system 1200 can include one or more processors 1202 which can control the operation of the computer system 1200. "Processors" are also referred to herein as "controllers." The processor(s) 1202 can include any type of microprocessor or central processing unit (CPU), including programmable general-purpose or special-purpose microprocessors and/or any one of a variety of proprietary or commercially available single or multi-processor systems. The computer system 1200 can also include one or more memories 1204, which can provide temporary storage for code to be executed by the processor(s) 1202 or for data acquired from one or more users, storage devices, and/or databases. The memory 1204 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 1200 can be coupled to a bus system 1212. The illustrated bus system 1212 is an abstraction that represents any one or more separate physical busses, communication lines/interfaces, and/or multi-drop or point-to-point connections, connected by appropriate bridges, adapters, and/or controllers. The computer system 1200 can also include one or more network interface(s) 1206, one or more input/output (IO) interface(s) 1208, and one or more storage device(s) 1210.

The network interface(s) 1206 can enable the computer system 1200 to communicate with remote devices, e.g., other computer systems, over a network, and can be, for non-limiting example, remote desktop connection interfaces, Ethernet adapters, and/or other local area network (LAN) adapters. The IO interface(s) 1208 can include one or more interface components to connect the computer system 1200 with other electronic equipment. For non-limiting example, the IO interface(s) 1208 can include high speed data ports, such as universal serial bus (USB) ports, 1394 ports, Wi-Fi, Bluetooth, etc. Additionally, the computer system 1200 can be accessible to a human user, and thus the IO interface(s) 1208 can include displays, speakers, keyboards, pointing devices, and/or various other video, audio, or alphanumeric interfaces. The storage device(s) 1210 can include any conventional medium for storing data in a non-volatile and/or non-transient manner. The storage device(s) 1210 can thus hold data and/or instructions in a persistent state, i.e., the value is retained despite interruption of power to the computer system 1200. The storage device(s) 1210 can include one or more hard disk drives, flash drives, USB drives, optical drives, various media cards, diskettes, compact discs, and/or any combination thereof and can be directly connected to the computer system 1200 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 19 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 1200 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 1200 can also include a web server for generating and/or delivering the web pages to client computer systems.

In an exemplary embodiment, the computer system 1200 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components of the systems and devices described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical method, comprising:
    actuating a homing mechanism to constrain an end effector coupled to a distal end of a shaft of a surgical tool coupled to a robotic surgical system to thereby substantially limit articulation of the end effector relative to the shaft, the homing mechanism having a fork member and a push rod that moves distally into the fork member to cause the fork member to lockingly engage at least one linkage member operably coupled to the end effector;
    applying, by at least one motor, a first force to the at least one linkage member to attempt articulation of the constrained end effector in a first direction until a resistance against further articulation exceeds a first threshold, and storing a first value of a force at which the resistance has exceeded the first threshold;
    applying, by the at least one motor, a second force to the at least one linkage member to attempt articulation of the constrained end effector in a second direction that is opposite the first direction until a resistance against further articulation exceeds a second threshold, and storing a second value of a force at which the resistance has exceeded the second threshold;
    determining, by a processor, first and second articulation angles based on the first and second values; and
    averaging, by the processor, the first and second articulation angles to obtain a home position of the constrained end effector.

2. The surgical method of claim 1, wherein:
    the at least one linkage member comprises a first linkage member and a second linkage member;
    the first force is applied to the first linkage member; and
    the second force is applied to the second linkage member.

3. The surgical method of claim 1, wherein the at least one linkage member comprises a plurality of flexible cables.

4. The surgical method of claim 1, wherein determining the first and second articulation angles comprises correlating the first and second values with stored values of a force that can be applied to the at least one linkage member, each of the stored values being stored in association with a respective value of an articulation angle.

5. The surgical method of claim 1, wherein storing the first and second values comprises storing the first and second values in a memory associated with the robotic surgical system.

6. The surgical method of claim 1, further comprising applying a force to the at least one linkage member to cause at least a portion of the end effector to pivot relative to the shaft with reference to the home position of the end effector.

7. The surgical method of claim 1, wherein the home position of the end effector indicates a position of the end effector at which an articulation angle of the end effector with respect to the shaft is considered to be zero.

8. The surgical method of claim 1, wherein the first and second thresholds are predetermined thresholds known to the robotic surgical system.

9. A surgical tool configured to be coupled to a robotic surgical system, comprising:
    a tool shaft having an end effector coupled to a distal end thereof;
    a wrist disposed between the tool shaft and the end effector;
    at least one linkage member associated with the tool shaft and operably coupled to the end effector such that force selectively applied to the at least one linkage member is able to cause at least one of a pitch and a yaw motion of the end effector; and
    a homing mechanism configured to be actuated to angularly adjust a presumed zero position of the end effector relative to the tool shaft to an adjusted zero position of the end effector, wherein the homing mechanism includes a fork member and a push rod configured to move distally into the fork member to cause the fork member to lockingly engage the at least one linkage member.

10. The surgical tool of claim 9, wherein the end effector is configured to be moved with respect to the wrist with reference to the adjusted zero position.

11. The surgical tool of claim 9, wherein when the end effector is in the adjusted zero position relative to the tool shaft, the at least one linkage member is configured to have force applied thereto to attempt articulation of the end effector in at least one direction until a resistance against further articulation exceeds a threshold.

12. The surgical tool of claim 9, wherein the at least one linkage member comprises a plurality of flexible cables.

13. The surgical tool of claim 9, further comprising a memory configured to store a plurality of values of a force that can be applied to the at least one linkage member, each of the stored values being stored in association with a respective value of an articulation angle.

14. The surgical tool of claim 9, wherein the fork member comprises a plurality of teeth configured to engage a plurality of teeth formed on the at least one linkage member.

15. The surgical tool of claim 14, wherein the homing mechanism is configured to angularly adjust the presumed zero position of the end effector by causing the teeth of the fork member to engage the teeth formed on the at least one linkage member such that the at least one linkage member is disposed at one of a plurality of predetermined positions with respect to the homing mechanism.

* * * * *